(12) United States Patent
Liu et al.

(10) Patent No.: US 8,131,336 B2
(45) Date of Patent: Mar. 6, 2012

(54) AUTOMATED IN VIVO PLAQUE COMPOSITION EVALUATION

(75) Inventors: Fei Liu, Seattle, WA (US); William S Kerwin, Seattle, WA (US); Dongxiang Xu, Seattle, WA (US); Chun Yuan, Bellevue, WA (US)

(73) Assignee: University of Washington, Seattle, WA (US)

(*) Notice: Subject to any disclaimer, the term of this patent is extended or adjusted under 35 U.S.C. 154(b) by 1314 days.

(21) Appl. No.: 11/445,510

(22) Filed: Jun. 1, 2006

(65) Prior Publication Data
US 2008/0009702 A1     Jan. 10, 2008

(51) Int. Cl.
    *A61B 5/05*     (2006.01)
(52) U.S. Cl. ......... 600/407; 600/410; 600/425; 382/173
(58) Field of Classification Search ............... 600/410, 600/407, 425; 382/173, 128, 131
    See application file for complete search history.

(56) References Cited

U.S. PATENT DOCUMENTS

| | | | | |
|---|---|---|---|---|
| 5,570,430 | A * | 10/1996 | Sheehan et al. | 382/128 |
| 2003/0053667 | A1* | 3/2003 | Paragios et al. | 382/128 |
| 2007/0053589 | A1* | 3/2007 | Gering | 382/173 |
| 2009/0129671 | A1* | 5/2009 | Hu et al. | 382/173 |

OTHER PUBLICATIONS

Clarke, S, et al, Validation of Automatically Classified Magnetic Resonance Images for Carotid Plaque Compositional Analysis, Stroke, (Jan. 2006), 37, 93-97.*
Clarke, S, et al, Quantitative Assessment of Carotid Plaque Composition using Multicontrast MRI and Registered Histology, Magnetic Resonance in Medicine, 50 : 1199-1208 (2003).*
Adame, I.M., et al., "Automatic Segmentation and Plaque Characterization in Atherosclerotic Carotid Artery MR Images," *MAGMA* 16:227-234, 2004.
Cheng, J., and R. Greiner, "Learning Bayesian Belief Network Classifiers: Algorithms and System," *Proceedings of the 14th Biennial Conference of the Canadian Society on Computational Studies of Intelligence*: Advances in Artificial Intelligence, Ottawa, Canada, Jun. 7-9, 2001, 10 pages.
Clarke, S.E., et al., "Quantitative Assessment of Carotid Plaque Composition Using Multicontrast MRI and Registered Histology," *Magnetic Resonance in Medicine* 50:1199-1208 (2003).
Itskovich, V.V., et al., "Quantification of Human Atherosclerotic Plaques Using Spatially Enhanced Cluster Analysis of Multicontrast-Weighted Magnetic Resonance Images," *Magnetic Resonance in Medicine* 52:515-523, 2004.
Ronen, R.R., et al., "Resolution and SNR Effects on Carotid Plaque Classification," *Magnetic Resonance in Medicine* 56:290-295, 2006.
Salvado, O., et al., "Method to Correct Intensity Inhomogeneity in MR Images for Atherosclerosis Characterization," *IEEE Transactions on Medical Imaging* 25(5):539-552, May 2006.

* cited by examiner

*Primary Examiner* — Brian Casler
*Assistant Examiner* — Daniel Huntley
(74) *Attorney, Agent, or Firm* — Christensen, O'Connor, Johnson, Kindness PLLC

(57) ABSTRACT

A method for the automated segmentation of in vivo image data is disclosed. A region of carotid artery in a number of patients was imaged using MRI. Histological data for each imaged region was then obtained, identifying various atherosclerotic plaque components in the imaged region. A portion of the histological data, and the image data, was used to generate PDFs based on image intensity, and on morphological data (local wall thickness and distance from lumen). The remaining data was used to validate the method. A plurality of MRI images were taken at various weightings, and the images were registered and normalized. The lumen and outer wall boundary were identified. The PDFs were combined in a Bayesian analysis with the intensity and morphological data to calculate the likelihood that each pixel corresponded to each of four plaque components. A contour algorithm was applied to generate contours segmenting the images by composition.

27 Claims, 1 Drawing Sheet

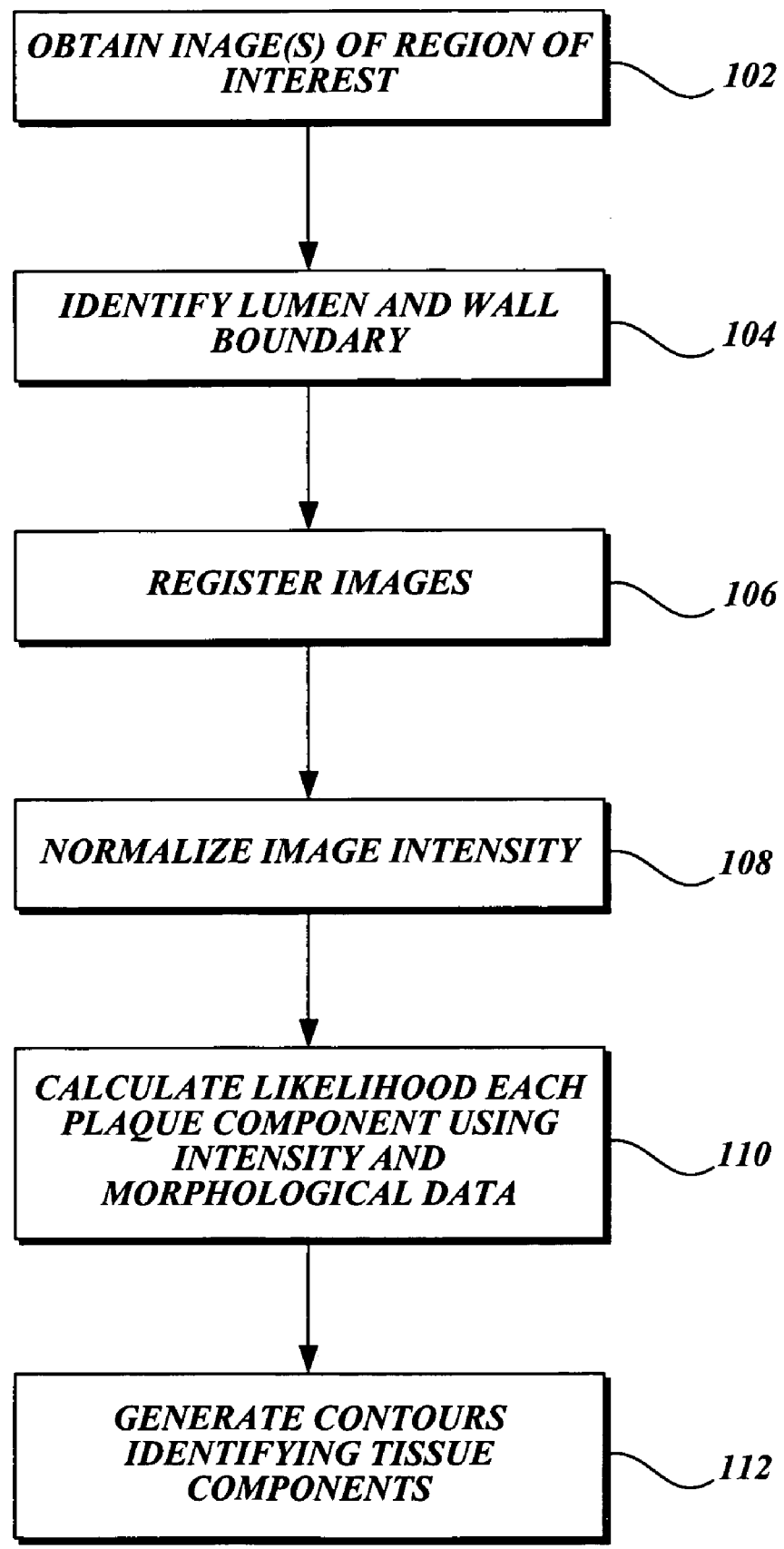

AUTOMATED IN VIVO PLAQUE COMPOSITION EVALUATION

STATEMENT OF GOVERNMENT LICENSE RIGHTS

Research leading to the present invention was supported, at least in part, under National Institute of Health Grant No. R44-HL070506. The Government may have certain rights in the invention.

BACKGROUND

Atherosclerosis, characterized by clogging, narrowing, and hardening of the body's large arteries and medium-sized blood vessels, can lead to stroke, heart attack, eye problems and kidney problems. It is a leading cause of mortality and morbidity worldwide. Growing evidence suggests that an important factor in assessing the increased risk associated with an atherosclerotic plaque deposit is the physical composition of the plaque. Indeed, the plaque composition is a better indicator of risk than the degree of luminal narrowing as measured by angiography.

Atherosclerosis is characterized by the deposition of plaques containing cholesterol and lipids on the innermost layer of the walls of arteries. Atherosclerosis is currently understood to be a chronic inflammatory disease rather than an inevitable degenerative aging process. The condition usually affects large- and medium-sized arteries. Although such plaque deposits can significantly reduce the blood's flow through an artery, the more serious risk is generally associated with the instigation of an acute clinical event through plaque rupture and thrombosis. In particular, serious damage can occur if an arterial plaque deposit becomes fragile and ruptures, fissures, or ulcerates. Plaque rupture, fissure, or ulcer can cause blood clots to form that block or occlude blood flow and/or break off and travel to other parts of the body. If such blood clots block a blood vessel that feeds the heart, it causes a heart attack. If the blood clot blocks a blood vessel that feeds the brain, it causes a stroke. Similarly, if blood supply to the arms or legs is reduced, it can cause difficulty in walking or light exercise and other collateral damage.

The presence and extent of plaque build up in an individual's arteries can be detected using a variety of techniques that are well known in the field including, for example, magnetic resonance imaging ("MRI"), computed tomography ("CT"), X-ray angiography, and ultrasound. Prior art methods for assessing an individual's risk of a clinically significant event such as a stroke or heart attack related to atherosclerotic deposits in an individual's arteries have primarily been directed to evaluating the effect that the plaque deposit has on the blood flow through the artery.

The risk associated with rupture, fissure, or ulceration of plaque, however, may be present even when the plaque deposit does not significantly reduce the flow of blood in an artery. For example, arteries and other blood vessels will sometimes expand or "remodel" in the region of a significant atherosclerotic plaque deposit such that the lumen area does not decrease sufficiently to significantly reduce blood flow. If the plaque ruptures, it may nevertheless create a blood clot that may travel to a critical area to cause a clinical event. The susceptibility of a plaque deposit to structural failure is difficult to determine.

Numerous studies have shown that MRI can detect differences in plaque composition, but that combined information from images with multiple contrast weightings is critical for distinguishing all plaque components. Desirable combinations of contrast weightings and a set of image characteristics have emerged that can be used to segment plaque into its subcomponents. Manual segmentation using these characteristics has produced quantitative measurements of the relative volumes of necrotic cores, calcification, loose matrix and fibrous tissue that correlate strongly with histological assessments. Efforts have been made to automate the segmentation of plaque components, focusing on the intensity characteristics of the plaque in the clinical images. Although somewhat successful in experiments on specimens imaged ex vivo, these methods have failed in vivo.

There remains a need for a relatively simple method and system for automating the identification and segmentation of the composition of an atherosclerotic plaque deposit in a patient's artery.

SUMMARY

This summary is provided to introduce concepts in a simplified form that are further described below in the detailed description. This summary is not intended to identify key features of the claimed subject matter.

A method is disclosed for the automated identification of composition for an internal body region based on medical images taken of the region. The method has been found effective, for example, for identifying the components in atherosclerotic plaque in an artery, such as the carotid artery.

One or more images of the region of interest are obtained. In a disclosed method, four MRI images, taken at different weightings, are used. The images include intensity data as well as morphological data, e.g., location information for points relative to key features in the region of interest. For example, a location in the region represented by a particular pixel may be characterized by the local wall thickness and distance from the imaged lumen.

A probability density function correlating image intensity information with the plaque components, and a probability function correlating image morphology information with the plaque components are then used to calculate a likelihood that each point in the image corresponds to the various plaque components. An a posterior Bayesian analysis may be used to generate these likelihood values.

The MRI images are preferably registered, to compensate for patient movement between images, and intensity-normalized. A contouring method, such as a competing active contour method, may then be used to generate contours segmenting the images according to composition.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

The FIGURE is a flow chart showing a particular embodiment of the method disclosed herein for automating the in vivo composition assessment of an imaged region.

DETAILED DESCRIPTION

Magnetic resonance imaging ("MRI") of atherosclerotic arteries is useful for identifying and characterizing internal plaque features, particularly when information from multiple contrast weightings is combined to distinguish the plaque components. Desirable combinations of contrast weighted images and a set of image characteristics have emerged that can be used to identify subcomponents in the imaged plaque. Typically, a trained specialist will manually analyze or segment the images to produce a quantitative assessment of the relative volumes of necrotic core, calcification, loose matrix, and fibrous tissue. Such manual assessments correlate well with histological assessments.

A method is disclosed herein for automating the identification and segmentation of medical images. Replacing subjective, manual segmentation with an automated segmentation alternative provides several benefits, including saving time in image review, reducing the considerable amount of clinician training required, and reducing intra-rater and inter-rater variability in such assessments. Additionally, a viable automated segmentation procedure allows various combinations of contrast weightings and image characteristics to be objectively analyzed for accuracy in plaque characterization, and may thereby provide for continued improvements in image analysis.

An automated, multi-contrast plaque segmentation technique is disclosed for assessing the plaque composition in vivo, using not only the image intensity data, but also morphological data to characterize the plaque composition. In particular, the currently preferred method uses a maximum a posteriori probability Bayesian method to statistically combine intensity and morphological data to more accurately identify compositional segments of the imaged region. The disclosed method is therefore referred to as "Morphology-Enhanced Probabilistic Plaque Segmentation" ("MEPPS").

Study Population

To develop and validate the present method, a total of thirty-one consecutive patients scheduled for carotid endarterectomy were imaged on a GE Signa 1.5 T MR scanner to obtain images with T1 (TR=800 ms, TE=11 ms), T2 (TR=3150 ms, TE=66 ms), proton density or PD (TR=2770 ms, TE=9.3 ms), time-of-flight or TOF (TR=23 ms, TE=2.8 ms) and contrast enhanced T1 or CE-T1 (TR=800 ms, TE=11 ms) weightings at ten contiguous locations, centered at the carotid bifurcation. CE-T1 images were acquired approximately ten minutes after injection of 0.1 mmol/kg of a gadolinium contrast agent. In-plane resolution was 0.63 mm, resulting in a pixel size of 0.31 mm after zero-filled interpolation, and the slice thickness was 2.0 mm.

At endarterectomy, the plaque was removed intact, formalin fixed, embedded en-bloc in paraffin, and serially sectioned at 1.0 mm intervals in the common carotid and at 0.5 mm intervals throughout the bulb and internal carotid. After staining, histology sections were matched to MR images using the bifurcation, lumen size and shape and calcifications as landmarks. The sections were digitized and regions of necrotic core (including interplaque hemorrhage), calcification, and loose matrix were outlined. All remaining tissue was considered as dense fibrous matrix.

The MR images were graded for quality, and five subjects were excluded for poor image quality. From the remaining subjects, a total of 142 locations were selected for study. To generate ground truth for training and evaluation of the segmentation algorithm, images from all 26, subjects were manually segmented based on established MRI criteria and knowledge of the histological results. Three types of tissue—calcification, necrotic core and loose matrix—were identified and the remainder was considered to be fibrous tissue.

From this data set, fourteen subjects (84 locations) were assigned to a training set and twelve subjects (58 locations) were assigned to a testing data set.

Segmentation Algorithm

Data for the 84 locations in the training set were used to generate the probability density functions that are used in the MEPPS algorithm, described below. The MEPPS algorithm first determines the probability that each point or pixel in the imaged region comprises each of the four tissue types, and then a competing active contours algorithm is used to generate optimal boundaries for each tissue type.

Pre-Processing

There are significant hurdles for in vivo plaque analysis compared to ex vivo analysis. For example, in vivo images are subject to patient motion, intensity inhomogeneities, and variable absolute intensities depending on relative coil placement. In the currently preferred method, the in vivo images are registered, the intensity adjusted relative to a uniform baseline, and the wall region identified, as discussed below.

Because of superior flow suppression from its double inversion recovery preparation, the T1 weighting was used for identifying the lumen and wall boundaries. Although in developing the present method the lumen and wall boundaries were traced manually, it is contemplated that automated identification of such features may alternatively be utilized. An exemplary automated method for identifying the lumen and vessel wall is disclosed in U.S. Provisional Patent Application No. 60/784,602, which is hereby incorporated by reference in its entirety.

Images from the remaining four weightings were then registered to the T1 weighted images, to compensate for patient motion between image acquisitions. The wall boundaries were also mapped to the remaining contrast weightings, precluding the need to independently obtain boundaries for all contrast weightings.

The effects of coil inhomogeneity were eliminated by dividing each image by a smooth, estimated sensitivity profile. The sensitivity profile was estimated within a 4 cm×4 cm region of interest aligned with the center of the wall contour using an adaptive threshold technique that simultaneously estimates the profile in all image weightings assuming they are related by a scalar multiple. Using a Neumann boundary condition, the profile u was estimated from observed signal g by solving the partial differential equation:

$$\Delta \log(u) + \lambda (\log(u) - \log(g)) \exp((-(\log(u) - \log(g))^2 / \sigma^2)) = 0$$

To normalize the absolute intensity, the image intensities for each image weighting is divided by its median intensity within the 4 cm×4 cm region described above. A typical prior art practice is to use the intensity of the adjacent sternocleidomastoid muscle or fibrous tissue to identify an iso-intense reference for normalizing signal intensity in manual review. The median intensity used in the currently preferred embodiment has been found to fall within the intensity range in the fibro-muscular region, whereas the mean intensity is highly dependent on the distribution between bright and dark pixels. The median value used herein has the advantage that it is easily obtained, without the need to detect a reference region in the image, and closely agrees with the image intensity of the sternocleidomastoid muscle.

Probability Map Generation

In the current embodiment, the MEPPS algorithm assigns four probabilities to each pixel, each probability representing the likelihood that the pixel corresponds to a location of necrotic core, calcification, loose matrix or fibrous tissue. These four probabilities are based on the pixel intensity, x, in each contrast weighting, and on two morphological factors: the local wall thickness t and the distance from the lumen d. Therefore, the probability may be represented as $Pr(T_i|[t,d],$ x), where $T_i$ corresponds to one of the four tissue types. The two distances t and d capture information about the local plaque morphology that also correlates with the tissue type. For example, thin plaque regions are generally fibrous, and loose matrix is most commonly seen adjacent to the lumen.

To estimate each probability, we assume that the image intensity for a given tissue does not vary with its position in the plaque. For example, calcification has the same appearance whether it is adjacent to the lumen or located more deeply within the plaque. Thus, x is conditionally independent of t and d, given $T_i$. This assumption allows the probability to be cast as a naïve-Bayesian network, and leads to the formula:

$$Pr(T_i \mid [t, d], x) = \frac{p([t, d] \mid T_i)p(x \mid T_i)Pr(T_i)}{\sum_{j=1}^{4} p([t, d] \mid T_j)p(x \mid T_j)Pr(T_j)}$$

The two conditionally independent probability density functions ("PDFs"), $p(x|T_i)$ and $p([t,d]|T_i)$, and the relative frequency of each of the four tissue types $Pr(T_i)$ were estimated from the training set. Factoring the probability in this way greatly reduces the required size of the training set and eliminates the need to estimate $Pr(T_i|[t,d],x)$ directly, which makes it possible to combine more features together given a limited data set.

To estimate the PDFs from the training set of 84 locations, a Parzen window method was used. In this method, a smooth PDF is estimated from a finite data set by using a Gaussian kernel to blur each data point in space. For $p(x|T_i)$, a Gaussian kernel of width $\sigma$=0.07 and computation of the PDF on a 5-dimensional grid with ten intensity levels per contrast weighting produced a smooth, self-consistent PDF. From this estimate, the PDF at an arbitrary point in space may be computed using linear interpolation over the grid. To estimate $p([t,d]|T_i)$ the Parzen window method was also used with $\sigma$=0.09 and eleven levels in the range of 0-6 mm.

Although the currently preferred embodiment uses probability density functions to correlate the image intensity and morphological data with the histologically-obtained composition data, it is contemplated that other methods or relations may be used to correlate the data with the image information. For example, a segmentation approach may use intensity thresholds to classify composition represented by a pixel. It is contemplated that the present invention might be practiced by using the morphological information to adjust such threshold values.

Contour Generation

Once the probabilities for each image pixel are calculated, each pixel is classified as corresponding to a particular tissue type. Although the pixels could be classified based on the highest probability alone, in the current embodiment of the method, a competing contour formulation is used to define the final regions identifying tissue types. This additional step provides two benefits: First it provides the ability to easily edit the regions by modifying contours; and second, it helps to eliminate isolated pixels and convoluted regions attributable to noise.

The contours delineating each tissue region are determined using the competing active contours, in an active region method, generally as described in *Coupled Geodesic Active Regions for Image, Segmentation: A Level Set Approach*, Paragios, N., and R. Deriche, *Proc. ECCV*, Dublin, Ireland, 224-240, 2000, which is hereby incorporated by reference in its entirety. Although the active region method is currently preferred, it will be readily appreciated that any suitable contour-generating algorithm may alternatively be used without departing from the present invention, or the raw pixel calculations may be used without any attempt at smoothing. In the active region method, as applied to the present application, each of four contours seeks one pre-assigned tissue. In order to produce reasonable boundaries, contours move under a smoothness constraint to maximize the total probability for corresponding tissue within the contour. Based on Gibbs-Markov random field theory, using the level set method to represent each contour, the energy functional is designed as:

$$E(\Phi_i) = \sum_{i=1}^{4} \int\int_{\Omega} -\log(Pr(T_i))H(\Phi_i)dxdy + \lambda_1$$
$$\sum_{i=1}^{4} \int\int_{\Omega} |\nabla H(\Phi_i)|dxdy + \lambda_2 \left(\int\int_{\Omega}\sum_{i=1}^{4} H(\Phi_i) - 1\right)^2 dxdy$$

where $\Phi_i$ is level set function and $H(\Phi)$ is the Heaviside function. The first item sums probability within the contours, the second term is a measure of total contour length and the third term constrains each pixel to belong to one, and only one, contour. By using the level set method, topology changes of the curves are handled automatically, allowing individual contours to split and merge to form as many distinct regions as necessary. Our experience indicates that to avoid severe shrinkage $\lambda_1$ is optimally set to a relatively small value, approximately 0.01, and $\lambda_2$ is optimally set to about 2.25, which satisfies both region partition and numerical stability.

Validation

The MEPPS algorithm was validated using the 58 locations from 12 subjects in the testing data set. The algorithm was applied using all five contrast weightings and compared to the histologically confirmed drawings. As an additional comparison, we also performed segmentation using only intensity information, by deleting the morphology-based terms from the probability computation. This allowed us to assess the contribution of morphology to overall performance.

For overall validation, the correlation between automatic and histology-guided manual segmentation was examined. The areas of each tissue type in each of the 58 test locations were used for comparison and the results are compiled in Table 1. The overall performance of the non-parametric intensity-based segmentation is generally similar to the Gaussian classifier, with the exception that identifying calcification is significantly improved with the non-parametric technique. The benefits of using morphology in addition to intensity are apparent, given the higher correlations for MEPPS compared to either of the results based on intensity alone.

TABLE 1

| Tissue | Manual | Gaussian | Intensity-based | MEPPS |
| --- | --- | --- | --- | --- |
| Necrotic Core | 0.71 | 0.65 | 0.61 | 0.78 |
| Calcification | 0.76 | 0.64 | 0.78 | 0.83 |
| Loose matrix | 0.33 | 0.28 | 0.32 | 0.41 |
| Fibrous tissue | 0.78 | 0.71 | 0.69 | 0.82 |

When comparing the results of MEPPS with the histology guided drawing, we found the correlation for necrotic core and fibrous tissue to be relatively high. This is partially due to the fact that typical areas of necrotic core and fibrous tissue are larger than calcifications or loose matrix. Nevertheless, calcification attained a higher correlation because it is well-defined in histology and by MRI. The lower correlation for loose matrix can be attributed to its small size and the fact that it represents an aggregate of multiple possible tissues that may have slightly different MRI properties. The observed misclassification of loose matrix was generally associated with fibrous tissue, which is not surprising given that loose matrix may be considered a sub-class of fibrous tissue. Furthermore, if we combine the two into a combined fibrous group, we achieve a correlation of 0.85 with histology.

The classification accuracies for all pixels in the testing set are tabulated in Table 2 in terms of sensitivity and specificity. Values for automated and blinded manual segmentation are similar, with both exhibiting high specificities for all tissue types and high sensitivity for fibrous tissue. Sensitivities for necrotic core and calcification are good, whereas loose matrix has relatively low sensitivity. The somewhat lower sensitivities can be attributed in large part to this metric being pessimistic for small regions, such as most calcifications and loose matrix. This is illustrated by the fact that the segmentation results are in excellent qualitative agreement with the histology-guided results. In particular, the sensitivity for detecting calcified pixels is only 0.37 and that for loose matrix is only 0.73. This is due to the fact that for small regions, slight differences in the location of contours can lead to a large percentage of pixels that do not overlap.

TABLE 2

|  | MEPPS | | Manual | |
| --- | --- | --- | --- | --- |
|  | Sensitivity | Specificity | Sensitivity | Specificity |
| Necrotic core | 0.75 | 0.92 | 0.64 | 0.90 |
| Calcifications | 0.65 | 0.98 | 0.77 | 0.97 |
| Loose matrix | 0.51 | 0.97 | 0.37 | 0.99 |
| Fibrous tissue | 0.88 | 0.78 | 0.84 | 0.68 |

Therefore, according to the present invention, accurate division of atherosclerotic plaque into its constitutive components can be accomplished with in vivo imaging, for example magnetic resonance imaging, and automated segmentation. In particular, automated identification of the various components in the image may be accomplished by combining pixilated image information such as image intensity, with morphological information, such as the local wall thickness and distance from the lumen. In the currently preferred method, an a posterior Bayesian network is developed. Probability density functions are obtained correlating the tissue type to an image intensity vector, and correlating tissue type to a morphologically-based vector (wall thickness and distance to lumen), based on histological data. The PDFs are then combined to obtain a discretized probability or confidence level regarding the composition of the imaged region. The discretized probability information may then be combined, for example using a competing contours algorithm, to segment the imaged region according to the most probable composition.

Exemplary Embodiment

Referring now to the FIGURE, the steps in a current embodiment of the present invention are shown. In the method of the FIGURE, one or more clinical images are obtained 102 of the selected region. For example, a plurality of MRI images, using selected image weightings as described above, may be taken of the region of interest. For at least one of the images, the lumen and outer wall boundary are identified 104. This identification process may be done manually by a trained clinician, or may be automated. If multiple images are taken, the images are registered 106, to compensate for patient movement between imaging. The image intensities are then normalized 108. The probability or likelihood that each pixel is of the particular plaque compositional elements is then calculated 110. This calculation uses both the image intensity information and morphological information, such as the position of the pixel relative to the lumen, and the local thickness of the vessel wall. For example, a probability density function correlating the plaque composition with morphological data, and a second probability density function correlating the plaque composition with image intensity data, are used in a Bayesian schema to generate the likelihood estimates for each pixel. The imaged region is then segmented using contours that represent best estimates of the boundaries between various compositional elements 112. A competing active contours method, for example, has proven effective.

The disclosed method has been compared to conventional, manual segmentation, as well as with histological data, and has been found to segment imaged plaque regions approximately as accurately as manual segmentation. The use of morphological data in combination with image intensity data has therefore been found effective for accurately segmenting medical image data. Although the disclosed embodiment of the present invention is directed to compositionally segmenting atherosclerotic plaque regions using MRI image sets, it is contemplated that the method may be extended to other imaging modalities, and to interpreting medical image data for other clinical purposes, including for example in oncology and the like. Combining morphological data with conventional pixel image data (e.g., intensity) in a probabilistic manner, for example using an a posterior Bayesian network, provides clinically beneficial advances in the automated interpretation of medical image data.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for in vivo identification of components in an interior region of a body comprising:
   using a medical imaging apparatus, obtaining an image of an interior region of a body, wherein the interior region includes components from a list of components, the image having pixel intensity information for individual pixels in the image;
   identifying a morphological structure in the image;
   for the individual pixels in the image, determining a distance from the pixel to the morphological structure;
   obtaining a first relationship correlating pixel intensity information with the components in the list of components;
   obtaining a second relationship correlating distance from the pixel to the morphological structure with the components in the list of components; and
   calculating a likelihood that the individual pixels in the image correspond to the components in the list of components using the first and second relationships, the pixel intensity information and the distance from the pixel to the morphological structure.

2. The method of claim 1, wherein the first relationship is a first probability density function and the second relationship is a second probability density function.

3. The method of claim 2, wherein the image comprises a plurality of magnetic resonance images taken at different weightings.

4. The method of claim 3, further comprising the step of selecting a first image from the plurality of images and identifying the morphological structure on the first image.

5. The method of claim 4, wherein the interior region of the body comprises an artery, and further wherein the morphological structure comprises at least one of an artery wall and an artery lumen.

6. The method of claim 5, wherein the artery is a carotid artery.

7. The method of claim 5, wherein the list of components includes necrotic core, calcification, loose matrix, and fibrous tissue.

8. The method of claim 5, further comprising the step of registering the plurality of images to the first image.

9. The method of claim 8, further comprising the step of normalizing the intensity of each of the plurality of images.

10. The method of claim 9, wherein the step of normalizing the intensity of each of the plurality of images includes dividing the pixel intensities by an estimated sensitivity profile.

11. The method of claim 9, further comprising the step of obtaining a median intensity from a region of each image, and wherein the pixel intensity for each of the plurality of images is normalized by the median intensity.

12. The method of claim 9, wherein the likelihood that the individual pixels in the image correspond to the components in the list of components is calculated using a Bayesian network.

13. The method of claim 12, further comprising the step of calculating contours on the image identifying regions of each of the components in the list of components.

14. The method of claim 13, wherein the contours are calculated using a competing active contours technique.

15. The method of claim 1, wherein the medical imaging apparatus comprises a magnetic resonance imaging apparatus.

16. The method of claim 1, further comprising the step:
for the individual pixels in the image, determining a second distance associated with the pixel, and further wherein the second relationship correlates the pixel distance and the second distance with each of the components in the list of components.

17. The method of claim 16, wherein the second distance comprises the local artery wall thickness at the location of the individual pixel.

18. A method for in vivo identification of the components of plaque in an artery comprising:
using a medical imaging apparatus, obtaining a plurality of images of an artery using an imaging modality, the plurality of images having pixel intensity data for each pixel in the plurality of images;
identifying a lumen in each of the plurality of images;
for individual pixels in the plurality of images, determining a distance from the pixel to the lumen;
selecting a first image from the plurality of images and registering the plurality of images to the first image;
obtaining a first correlation relating pixel intensity values in images obtained by the imaging modality with atherosclerotic plaque components;
obtaining a second correlation relating pixel distance from the lumen with atherosclerotic plaque components; and
for individual pixels in the plurality of images, calculating a likelihood that the pixel corresponds to each of the atherosclerotic plaque components using the pixel intensity data and the first correlation with the pixel distance from the lumen and the second correlation.

19. The method of claim 18 wherein the first correlation comprises a first probability density function, and the second correlation comprises a second probability density function.

20. The method of claim 18, further comprising determining a local wall thickness of the artery, and wherein the second correlation further relates the local wall thickness to the components in the list of components.

21. The method of claim 18, wherein the imaging modality is magnetic resonance imaging.

22. The method of claim 18, wherein the plurality of images include at least four images taken at different image weightings.

23. The method of claim 19, wherein the first and second probability density functions are obtained by comparing image data for test regions with histological data for the same test regions.

24. The method of claim 18, further comprising the step of normalizing the pixel intensity data in the plurality of images.

25. The method of claim 24, wherein the pixel intensity data is normalized using a median intensity from a selected region of each of the plurality of images.

26. The method of claim 18, further comprising the step of calculating contours and estimating boundaries between components using the calculated likelihoods of each component for each pixel.

27. The method of claim 26, wherein the contours are calculated using a competing active contours method.

* * * * *

UNITED STATES PATENT AND TRADEMARK OFFICE
CERTIFICATE OF CORRECTION

PATENT NO. : 8,131,336 B2
APPLICATION NO. : 11/445510
DATED : March 6, 2012
INVENTOR(S) : F. Liu et al.

It is certified that error appears in the above-identified patent and that said Letters Patent is hereby corrected as shown below:

| COLUMN | LINE | ERROR |
|---|---|---|
| 1 | 7-10 | "Research leading to the present invention was supported, at least in part, under National Institute of Health Grant No. R44-HL070506. The Government may have certain rights in the invention." should read --This invention was made with government support under R44-HL070506 awarded by the National Institutes of Health. The government has certain rights in the invention.-- |

Signed and Sealed this
Nineteenth Day of February, 2013

Teresa Stanek Rea
*Acting Director of the United States Patent and Trademark Office*